United States Patent
Belhaj et al.

(10) Patent No.: US 12,251,455 B2
(45) Date of Patent: Mar. 18, 2025

(54) HIGH OIL CONTENT TOPICAL PERSONAL CARE PRODUCTS

(71) Applicant: CARGILL, INCORPORATED, Wayzata, MN (US)

(72) Inventors: Nabila Belhaj, Saint Cloud (FR); Jean-Noel Ollagnier, Evere (BE)

(73) Assignee: CARGILL, INCORPORATED, Wayzata, MN (US)

( * ) Notice: Subject to any disclaimer, the term of this patent is extended or adjusted under 35 U.S.C. 154(b) by 792 days.

(21) Appl. No.: 17/440,355

(22) PCT Filed: Mar. 13, 2020

(86) PCT No.: PCT/US2020/022586
§ 371 (c)(1),
(2) Date: Sep. 17, 2021

(87) PCT Pub. No.: WO2020/190697
PCT Pub. Date: Sep. 24, 2020

(65) Prior Publication Data
US 2022/0192948 A1    Jun. 23, 2022

Related U.S. Application Data

(60) Provisional application No. 62/910,579, filed on Oct. 4, 2019, provisional application No. 62/820,441, filed on Mar. 19, 2019.

(51) Int. Cl.
*A61K 8/362* (2006.01)
*A61G 17/04* (2006.01)
*A61K 8/73* (2006.01)
*A61Q 17/04* (2006.01)

(52) U.S. Cl.
CPC .............. *A61K 8/362* (2013.01); *A61G 17/04* (2013.01); *A61K 8/73* (2013.01); *A61K 8/732* (2013.01)

(58) Field of Classification Search
None
See application file for complete search history.

(56) References Cited

U.S. PATENT DOCUMENTS

| | | | |
|---|---|---|---|
| 9,744,114 B2 | 8/2017 | Russell et al. | |
| 2005/0208009 A1* | 9/2005 | Bonnardel | C08L 3/06 424/70.13 |
| 2006/0280714 A1 | 12/2006 | Maningat | |
| 2012/0121519 A1 | 5/2012 | Thomaides | |
| 2014/0287128 A1 | 9/2014 | Saito et al. | |

FOREIGN PATENT DOCUMENTS

| | | |
|---|---|---|
| CN | 1672780 A | 9/2005 |
| CN | 103327959 A | 9/2013 |
| EP | 1584370 B1 | 9/2014 |
| JP | 2005270975 A | 10/2005 |
| JP | 2018507911 A | 3/2018 |
| WO | 2013084848 A1 | 6/2013 |
| WO | 2016138357 A1 | 9/2016 |

OTHER PUBLICATIONS

Database GNPD [Online] MINTEL; Jul. 6, 2016 (Jul. 6, 2016), anonymous: "Aloe Vera Hair Mask", NP055695779, retrieved from www.gnpd.com, Database accession No. 4125609.

* cited by examiner

*Primary Examiner* — Dominic Lazaro

(57) ABSTRACT

The present invention relates to the production of personal care products that have a high oil content. Specifically the use of a novel combination of starches which allows for the manufacturing of high oil compositions that maintain desirable high quality sensory characteristics. Compositions include cosmetic and personal care items such as lotions and creams.

25 Claims, No Drawings

HIGH OIL CONTENT TOPICAL PERSONAL CARE PRODUCTS

CROSS-REFERENCE TO RELATED APPLICATIONS

This application is a national phase of International Application No. PCT/US2020/022586, filed Mar. 13, 2020, which claims the benefit of U.S. Provisional Patent Application No. 62/910,579, filed Oct. 4, 2019 and U.S. Provisional Patent Application No. 62/820,441, filed Mar. 19, 2019, each of which is hereby incorporated by reference in its entirety.

FIELD OF INVENTION

The present invention relates to the production of personal care products that have a high oil content. Specifically the use of a novel combination of starches which allows for the manufacturing of high oil compositions that maintain desirable high quality sensory characteristics.

BACKGROUND

There is a lack of solution on the cosmetic market concerning natural emulsifiers that are able to create oil in water emulsion with high oil content (above 30%). Personal care products are often an oil-in-water emulsion. These emulsions must be stable over time and provide a desirable experience to the consumer when they are used and applied. Typically, when oil content of a personal care product is above 30%, synthetic stabilizers or emulsifiers are required, and the product has an unacceptable greasy or oily feeling that lingers on the skin, especially with vegetable oils. While higher oil content products are desired for a number of functional reasons, this sensory challenge limits the ability of manufactures to develop products with high oil content. The present invention allows manufacturers to address this market need with naturally derived products. The combination of HP and nOSA starches when used at a specific ratio as described herein allows for the preparation of stable high oil formulations with desirable sensory characteristics.

SUMMARY OF INVENTION

The present invention provides a topical formulation comprising a starch component wherein the starch component comprises a nOSA starch and a HP starch wherein
  a. the nOSA starch and HP starches are present in the formulation at concentration of 2-10% and
  b. the ratio of nOSA to HP starch is between 3:1 and 20:1.

DETAILED DESCRIPTION

Explanations of abbreviations and terms used in this disclosure are provided to assist in comprehending and practicing the invention.

All ratios of emulsion or formulation components refer to percentage by weight (wt %), unless otherwise specified.

All parameter ranges disclosed include the end-points and all values in between, unless otherwise specified.

Representative features are set out in the following description, which stand alone or may be combined, in any combination, with one or more features disclosed elsewhere in the description and/or drawings of the specification.

When used in this specification and claims, the terms "comprises" and "comprising" and variations thereof mean that the specified features, steps or integers are included. The terms are not to be interpreted to exclude the presence of other features, steps or components.

Starches

A modified starch has a structure that has been altered from its native state, resulting in modification of one or more of its chemical or physical properties. Starches may be modified, for example, by enzymes, oxidation or, substitution with various compounds. For example, starches can be modified to increase stability against heat, acids, or freezing, improve texture, increase or decrease viscosity, increase or decrease gelatinization times, and/or increase or decrease solubility, among others. Modified starches may be partially or completely degraded into shorter chains or glucose molecules. Amylopectin may be debranched. In one example, modified starches are cross-linked for example to improve stability. Starches that are modified by substitution have a different chemical composition. A nOSA starch is a modified starch that has been partially substituted, e.g., from about 0.1% to about 3%, with n-octenyl succinic anhydride. Preferred nOSA starches of the present invention include C*EmTex 12688 (sodium starch octenylsuccinate) commercially available from Cargill Incorporated. A hydroxypropylated starch (HP starch) is another example of a modified starch that has been functionalized by hydroxypropylation. Such hydroxypropylated starches are well known in the art and are "E-coded" under the designation 1400 in the International System for Food Additives (INS). Preferred hydroxypropylated starches of the present invention include C*HiForm 12748 commercially available from Cargill incorporated.

Emulsion

In one aspect, the present invention is a high content oil-in-water emulsion. An emulsion may be defined as a mixture containing two immiscible liquids, in which one liquid is dispersed as droplets or globules throughout the other. The dispersed liquid is called the dispersed phase, while the other liquid is called the continuous phase. In an oil-in-water emulsion, as in the present invention, the oil is the dispersed phase or oil phase, and water is the continuous phase or aqueous phase.

The emulsion has good stability, with little or no separation between the aqueous phase and oil phase over an extended period of time (e.g. 4, 8, or 12 weeks) when measured at room temperature and/or elevated storage temperatures (e.g. 45° C.). Therefore, it may be used to make products (e.g. topical formulations) requiring a long shelf life.

1. Aqueous Phase

The inventive emulsion contains an aqueous phase. The aqueous phase may comprise or consist of water, in particular a demineralized water; a floral water such as cornflower water; a mineral water such as Vittel water, Lucas water or La Roche Posay water; and/or a spring water. Preferably, demineralized water is used as the aqueous phase utilized by the present invention.

The amount of the aqueous phase in the emulsion may be between 95 wt % to 30 wt %. For example, the amount of the aqueous phase in the emulsion may be between 40 wt % to 70 wt %, preferably between 40 wt % to 60 wt %.

2. Oil Phase

The inventive emulsion also contains an oil phase dispersed in the aqueous phase. As used herein, the term "dispersion" refers to an oil phase forming droplets inside the aqueous phase. The droplets may have any sizes and shapes. Preferably, the droplets are homogeneously distributed throughout the aqueous phase. The nature of the oil phase of the emulsion is not critical. The oil phase may thus consist of any fatty substance conventionally used in the cosmetic or dermatological fields; in particular the oil phase may comprise at least one oil, i.e. any fatty substance that is in substantially or completely liquid form at room temperature (20-25° C.) or elevated temperate of (40-70° C.) and at atmospheric pressure (760 mmHg).

The preferred oil phase(s) comprises at least one oil which can be a hydrocarbon-based oil, i.e. an oil mainly containing hydrogen and carbon atoms and optionally oxygen, nitrogen, sulfur and/or phosphorus atoms, for example in the form of hydroxyl or acid radicals; a silicone oil, i.e. an oil comprising at least one silicon atom and preferably at least one Si—O group; a fluoro oil, i.e. an oil comprising at least one fluorine atom; a non-fluoro oil, or a mixture thereof. Preferably, the inventive emulsion comprises at least one hydrocarbon-based oil as the oil phase.

The hydrocarbon-based oils may be of animal origin or of vegetable origin, such as liquid triglycerides of fatty acids comprising from 4 to 20 carbon atoms, examples include, coconut oil, canola oil, rapeseed oil, sunflower oil; maize oil; soybean oil; cucumber oil; grape seed oil; sesame seed oil; hazelnut oil; apricot oil; macadamia oil; arara oil; castor oil; cocoa butter; almond oil; avocado oil; babassu oil; caprylic/capric acid triglycerides, such as those sold by Stearineries Dubois or those sold under the names Miglyol 810, 812 and 818 by Dynamit Nobel; Simmondsia Chinensis (Jojoba) Seed oil sold under the tradename Jojoba Oil Golden by Desert Whale; Beta-carotene sold under the tradename Betatene 30% OLV by Cognis (BASF); Rosa Canina Fruit Oil sold under the tradename Rosehip Seed Oil by Nestle World Trade Co.; shea butter oil; and mixtures thereof.

Preferably, the oil phase contains a vegetable oil and/or a vegetable fat; more preferably it contains coconut oil, more preferably it contains cocoa butter and a vegetable oil, e.g. almond oil; even more preferably, the oil phase contains caprylic/capric acid triglycerides, cocoa butter and a vegetable oil different that said triglycerides, e.g. almond oil.

The hydrocarbon-based oils may be linear or branched hydrocarbons of mineral or synthetic origin. Alternatively, the hydrocarbon-based oils may be synthetic ethers; synthetic esters; fatty alcohols that are liquid at room temperature, with a branched and/or unsaturated carbon-based chain containing from 12 to 26 carbon atoms; C12-C22 higher fatty acids; or mixtures thereof.

The high oil content emulsions of the present invention include emulsions with oil phase in the emulsion between 5 wt % to 70%. For example, the amount of oil phase in the emulsion may be between 30 wt % to 60 wt %, preferably between 40 wt % and 60 wt %.

The emulsion may further comprise at least one further ingredient. The further ingredient may include, without limitation, a preservative, salt, vitamin, emulsifier, texturiser, nutrient, micronutrient, sugar, protein, polysaccharide, polyol, glucose, sucrose, glycerol, sorbitol, pH adjusters, emollients, dyes, pigments, skin actives, waxes or silicones.

Topical Formulation

The emulsion provided herein is useful in the manufacture of topical formulations such as personal care products or cosmetics. The inventors unexpectedly found that formulations comprising a combination of specific ratio of ratios of sodium starch octenylsuccinate and hydroxypropyl starch phosphate have numerous desirable characteristics as explained further below.

In one aspect, the present invention is a topical formulation comprising an emulsion as described herein. As used herein, the term "topical formulation" refers to a formulation that may be applied directly to a part of the body. The term "formulation" is used herein to denote compositions of various ingredients in various weight ranges, in accordance with the present invention.

The formulations manufactured with the emulsions described herein are suitable for use on hair, scalp, nails and skin, for delivering cosmetic or actives to the skin or hair for providing cleansing, conditioning, moisturizing, minimizing or treating skin imperfections, reducing skin oiliness, providing fragrances to the hair or skin and the like.

"Personal care" means and comprises any cosmetic, hygienic, toiletry and topical care products including, without limitation, leave-on products (i.e., products that are left on keratinous substrates after application); rinse-off products (i.e., products that are washed or rinsed from keratinous substrates during or within a few minutes of application); shampoos; hair curling and hair straightening products; hair style maintaining and hair conditioning products; lotions and creams for nails, hands, feet, face, scalp and/or body; hair dye; face and body makeup; nail care products; astringents; deodorants; antiperspirants; anti-acne; antiaging; depilatories; colognes and perfumes; skin protective creams and lotions (such as sunscreens); skin and body cleansers; skin conditioners; skin toners; skin firming compositions; skin tanning and lightening compositions; liquid soaps; bar soaps; bath products; shaving products; and oral hygiene products (such as toothpastes, oral suspensions, and mouth care products).

The texture of such personal care formulations is not limited and may be, without limitation, a liquid, gel, spray, emulsion (such as lotions and creams), shampoo, pomade, foam, tablet, stick (such as lip care products), makeup, suppositories, among others, any of which can be applied to the skin or hair or hale and which typically are designed to remain in contact therewith until removed, such as by rinsing with water or washing with shampoo or soap. Other forms could be gels that can be soft, stiff, or squeezable. Sprays can be non-pressurized aerosols delivered from manually pumped finger-actuated sprayers or can be pressurized aerosols such as mousse, spray, or foam forming formulation, where a chemical or gaseous propellant is used.

The topical formulation comprising the emulsion disclosed herein may be a cream. Advantageously, the cream may comprise specific ratio of ratios of sodium starch octenylsuccinate and hydroxypropyl starch phosphate.

Formulations prepared using the emulsion disclosed herein have a white or pale white color that is generally considered to be aesthetically appealing. In some cases, the formulations of the invention may be further processed to make a coloured end product. In such cases, the white colour is beneficial because it will show up the additional pigment without influencing the final colour.

Furthermore, formulations prepared using the ingredients of the present invention have a good spreadability with powdery and less greasy residual feeling on the skin. Even with high oil content, the ingredient absorb the fatty film at the skin surface. The use of the ingredients of the present invention improve creaminess, body and formula gloss. This texture feels pleasant to touch and apply. Furthermore, the consistency is such that good product pick-up may be achieved. Good product pick-up means that sufficient product (i.e. not too much, and not too little) can be collected on the user's finger.

Emulsions may optionally contain at least one further ingredient chosen from the group consisting of preservative, salt, vitamin, emulsifier, texturiser, nutrient, micronutrient, sugar, protein, polysaccharide, polyol, glucose, sucrose, glycerol, sorbitol, pH adjusters, emollients, dyes, pigments, skin actives, waxes, or silicones.

The emulsions of the present disclosure are particularly useful in sunscreen applications. Sun screens contain ingredients intended to block UV radiation from reaching the skin. UV blockers can be physical such as or chemical salts like ZnO or TiO2 or chemical (max authorized level indicated) such as Butyl Methoxydibenzoylmethane (5%); Octocrylene (10%); Titanium dioxide (25%); Ethylhexyl Salicylate (5%); Ethylhexyl Methoxycinnamate (10%); Bis-ethylhexyloxyphenol Methoxyphenyl Triazine (10%); Emulsions of the present disclosure can be used with any type of UV blocker know in the art or mixtures of UV blockers.

A representative example of a sunscreen is set out below. The phases are prepared separately and mixed together sequentially. The phases are blended at room temperature, by processes well known in the art. Typically high shear mixing is used to ensure creation of complete emulsion. At room temperature, add phase A to the phase B under a rotor stator homogenization (4 min at 4000 rpm). Slow addition of the phase C while mixing at around 9000 rpm until perfect homogenization. Phase D is added at the end with mixing.

embodiment the blend further comprises a texturizer. Texturizers including but not limited to carrageenan, cellulose and its derivatives, synthetic polymers like acrylates and carbomer, sclaroglucan, and Xanthan gum are useful in the present invention. Preferred texturizers include but are not limited to sclaroglucan and Xanthan gum. Texturizers can be present in any useful or desired amount. Typically texturizers will be present in amount of 0.1-7% of the blend, preferably 0.5-5%.

The blend can be prepared according to blending methods for dry ingredients that are known in the art. Use of a standard mixing equipment for a sufficient time will easily prepare the blends described herein.

Example 1

Materials Include:
1) nOSA starch [*C*EmTex* 12688: Under the International Nomenclature of Cosmetic Ingredients (INCI): Sodium starch octenylsuccinate)].
2) HP Starch [*C*HiForm* 12748: Under the International Nomenclature of Cosmetic Ingredients (INCI): Hydroxypropyl starch phosphate]

Step 1: The starches in the appropriate ratio and in an amount necessary to (2, 4, or 6%) of the final emulsion were mixed with a mass of oil that represented 8% of the total oil utilized in the final emulsion.

| Phase | Trade name | Supplier | INCI name | % WT | Grams (Th.) | Grams (Exp.) |
|---|---|---|---|---|---|---|
| A | 80/20 blend of NOSA/HP Starch of the present disclosure. | CARGILL | Sodium starch octenylsuccinate & Hydroxypropyl starch phosphate | 3.00% | 6.00 | 6.05 |
| | ACTIGUM VSX 20 | CARGILL | Sclerotium Gum & Xanthan Gum | 0.40% | 0.80 | 0.80 |
| | STAR DESIGN CARE | CARGILL | Hydroxypropyl starch phosphate | 2.00% | 4.00 0.00 | 3.95 |
| B | WATER | NA | WATER | 64.10% | 128.20 | 128.00 |
| | GLYCERINE | GARGILL | GLYCERINE | 3.00% | 6.00 0.00 | 6.30 |
| C | PARSOL 1789 | DSM | Butyl Methoxydibenzoylmethane | 3.000% | 6.00 | 6.00 |
| | PARSOL 340 | DSM | Octocrylene | 2.70% | 5.40 | 5.43 |
| | PARSOL HMS | DSM | Homosalate | 15.00% | 30.00 | 29.80 |
| | PARSOL EHS | DSM | Ethylhexyl Salicylate | 5.00% | 10.00 | 10.20 |
| | TOCOPHERYL ACETATE | | TOCOPHERYL ACETATE | 0.50% | 1.00 0.00 | 1.05 |
| D | ALPHA TOCOPHEROL | CARGILL | ALPHA TOCOPHEROL | 0.10% | 0.20 | 0.20 |
| | PARFUM FLEUR D'oranger | SYMRISE | Benzyl Alcohol & Salicylic Acid & Glycerin & Sorbic Acid | 0.10% | 0.20 | 0.20 |
| | GEOGARD ECT | LONZA | | 1.00% | 2.00 | 2.00 |
| | DERMOFEEL PA 3 | | Sodium Phytate; Aqua; Alcohol | 0.10% | 0.20 | 0.20 |
| | TOTAL: | | | 100.00% | 200.0 | 200.2 |

Blend

As used herein, the term "blend" refers to a physical mixture of two or more substances. An alternative embodiment of the present invention comprises a blend of starches useful for preparations of the emulsions described herein. Advantageously, the emulsions of the present invention are manufactured using a blend comprising or consisting of sodium starch octenylsuccinate and hydroxypropyl starch phosphate. HP can present in the blend in an amount of 5-25%. Preferably nOSA is present in an amount of 15-25% in the blend. nOSA can present in the blend in an amount of 75-95%. Preferrably nOSA is present in an amount of 75-85% in the blend.

The starch blend and additionally contain other dry ingredients if desired in the final emulsions such at texturizers, colorants, favors, fragrances, and the like. In a preferred Step 2:
Sclerotium gum or Xanthan gum was added into the total water phase under vigorous agitation (1800 rpm). Mixing was sustained for approximately 15 min for total hydration of the polysaccharides and/or until a homogeneous phase was obtained.
After increasing agitation to 2000 rpm, starch premix (step 1) was added and mixed for approximately 15 min and/or until a homogeneous phase was obtained.

Step 3: After increasing agitation to 3000 rpm, the remaining oil phase was added slowly until the creation of the emulsion. Homogenization was maintained for approximately 2 min to achieve the emulsion).

Tested ratios of sodium starch octenylsuccinate/hydroxypropyl starch phosphate: 100-0, 80-20, 75-25, 50-50, 25-75, 0-100. Starch was included at 2, 4, and 6% of the total emulsion.

TABLE 1

| % Rapeseed Oil | Ratio* | % Starch mixture in the formulation | Viscosity Day 1 mPa · s | Observed Stability |
|---|---|---|---|---|
| 30 | 100-0 | 2 | R4; 20 rpm 5020 mPa · s (50.2%) | Stable 8 weeks @ RT & 40° C. |
|  | 80-20 | 2 | R5; 20 rpm 5380 mPa · s (26.9%) | Stable 4 weeks @ RT & 40° C. |
|  | 75-25 | 2 | R4; 20 rpm 4140 mPa · s (41.4%) | Stable 8 weeks @ RT & 40° C. |
| 30 | 100-0 | 4 | R5; 20 rpm 7080 mPa · s (35.4%) | Stable 8 weeks @ RT & 40° C. |
|  | 80-20 | 4 | R5; 20 rpm 9600 mPa · s (48.0%) | Stable 4 weeks @ RT & 40° C. |
|  | 75-25 | 4 | R5; 20 rpm 9560 mPa · s (47.8%) | Stable 8 weeks @ RT & 40° C. |
| 30 | 100-0 | 6 | R5; 20 rpm 8740 mPa · s (43.7%) | Stable 8 weeks @ RT & 40° C. |
|  | 80-20 | 6 | R6; 20 rpm 14000 mPa · s (28.0%) | Stable 4 weeks @ RT & 40° C. |
|  | 75-25 | 6 | R5; 20 rpm 15300 mPa · s (76.5%) | Stable 8 weeks @ RT & 40° C. |
| 50 | 100-0 | 2 | R6; 20 rpm 16550 mPa · s (33.1%) | Stable 8 weeks @ RT & 40° C. |
|  | 80-20 | 2 | R6; 20 rpm 12150 mPa · s (24.3%) | Stable 4 weeks @ RT & 40° C. |
|  | 75-25 | 2 | R6; 20 rpm 13950 mPa · s (27.9%) | Stable 8 weeks @ RT & 40° C. |
| 50 | 100-0 | 4 | R6; 20 rpm 18950 mPa · s (37.5%) | Stable 8 weeks @ RT & 40° C. |
|  | 80-20 | 4 | R6; 20 rpm 27250 mPa · s (54.5%) | Stable 8 weeks @ RT & 40° C. |
|  | 75-25 | 4 | R6; 20 rpm 27000 mPa · s (54.0%) | Stable 8 weeks @ RT & 40° C. |
| 50 | 100-0 | 6 | R6; 20 rpm 25800 mPa · s (51.6%) | Stable 8 weeks @ RT & 40° C. |
|  | 80-20 | 6 | R6; 20 rpm 31100 mPa · s (62.2%) | Stable 4 weeks @ RT & 40° C. |
|  | 75-25 | 6 | R7; 20 rpm 53000 mPa · s (26.5%) | Stable 8 2 weeks @ RT & 40° C. |
| 60 | 100-0 | 2 | R6; 20 rpm 23850 mPa · s (47.7%) | Stable 8 weeks @ RT & 40° C. |
|  | 80-20 | 2 | R6; 20 rpm 22350 mPa · s (44.7%) | Stable 8 weeks @ RT & 40° C. |
|  | 75-25 | 2 | R6; 20 rpm 21850 mPa · s (43.7%) | Stable 8 weeks @ RT & 40° C. |
| 60 | 100-0 | 4 | R6; 20 rpm 40250 mPa · s (80.2%) | Stable 8 weeks @ RT & 40° C. |
|  | 80-20 | 4 | R6; 20 rpm 47700 mPa · s (95.4%) | Stable 8 weeks @ RT & 40° C. |
|  | 75-25 | 4 | R6; 20 rpm 38450 mPa · s (76.9%) | Stable 8 weeks @ RT & 40° C. |
| 60 | 100-0 | 6 | R7; 20 rpm 74200 mPa · s (37.1%) | Stable 8 4 weeks @ RT & 40° C. |
|  | 80-20 | 6 | R7; 20 rpm 101000 mPa · s (50.7%) | Stable 8 weeks @ RT & 40° C. |
|  | 75-25 | 6 | R7; 20 rpm 101000 mPa · s (50.5%) | Stable 8 weeks @ RT & 40° C. |

*Ratio of Sodium starch octenylsuccinate/Hydroxypropyl starch phosphate

Acceptable stability was not achieved with any samples containing less than 75 percent of nOSA starch even as percentage of starch increased to 6%.

The addition of HP starch is critical to provide desirable high quality sensory characteristics. The dramatic increase in viscosity and the perception of greasiness and oily residual feeling is greatly reduced by the use of HP starch in the emulsion. The inclusion of HP starch also provides for a whiter and glossier appearance of the emulsions. Both whiteness and a glossy appearance are highly desirable to the end consumer.

Viscosity Measurement:

| Equipment | Brookfield Viscometer DV-II + Pro, Ametek, USA |
|---|---|
| Temperature | All samples were measured at room temperature (22-24° C.). |
| Details | 20 rpm 1-minute measurement |
| Measurement | Turn on the viscometer Select spindle number (1-7). Torque should be between 10 and 90% rpm set to 20 Inset the spindle, the sample should come to spindle mark After 1 minutes record the viscosity value, torque and spindle |

Stability

Stability is evaluated visually by observing the stability of the emulsion over time. The emulsion fails if the phases separate or begin to separate. Major pooling of oil or water droplets on the surface or a significant change in the visual color or texture of the samples would also indicate failure of the emulsion. In addition, viscosity could be rechecked and significant decrease (>20%) would indicate failure of the emulsion.

We claim:

1. A topical emulsion formulation comprising an oil phase, an aqueous phase, and a starch component,
   wherein the starch component comprises an n-octenyl succinic anhydride modified starch (nOSA starch) and a hydroxypropylated starch (HP starch),
   wherein the oil phase is present in the formulation at a concentration between 5% to 70% by weight;
   wherein the nOSA starch and HP starch are present in the formulation at a concentration of 2% to 10% by weight; and
   wherein the nOSA starch to HP starch are present in the formulation at a weight ratio that is between 3:1 and 20:1.

2. The formulation of claim 1 further comprising a texturizer.

3. The formulation of claim 2 wherein the texturizer comprises a sclaroglucan, a xanthan gum, or a mixture of both.

4. A cosmetic or personal care product comprising the formulation of claim 3.

5. The cosmetic or personal care product of claim 4 selected from the group consisting of a skin protective cream, a lotion, a sunscreen, a skin or body cleanser, a skin conditioner, a skin toner, and a skin firming composition.

6. The cosmetic or personal care product of claim 4, wherein the cosmetic or personal care product is a sunscreen.

7. The formulation of claim 3 comprising 30% to 60% by weight oil.

8. The formulation of claim 2, wherein the texturizer comprises xanthan gum.

9. The formulation of claim 2, wherein the texturizer comprises sclaroglucan.

10. The formulation of claim 1, wherein the weight ratio of nOSA starch to HP starch is between 3:1 and 10:1.

11. The formulation of claim 1 comprising 30% to 60% by weight of the oil phase.

12. The formulation of claim 1 comprising 50% to 60% by weight of the oil phase.

13. The formulation of claim 1, wherein the oil phase is present in the formulation at a concentration between 40 weight percent to 70 weight percent.

14. The formulation of claim 1, wherein the oil phase comprises a hydrocarbon-based oil.

15. The formulation of claim 1 wherein the oil phase comprises a triglyceride of a fatty acid having 4 to 20 carbon atoms that is a liquid at 20° C. to 25° C. or at an elevated temperature of 40° C. to 70° C.

16. The formulation of claim 1, wherein the oil phase is present in the formulation at a concentration between 30 weight percent to 60 weight percent.

17. The formulation of claim 1, wherein the oil phase is present in the formulation at a concentration between 40 weight percent to 60 weight percent.

18. An emulsion composition comprising an oil phase, an aqueous phase and a starch blend comprising an n-octenyl succinic anhydride modified starch (nOSA starch), a hydroxypropylated starch (HP starch), and a texturizer wherein:
   the oil phase is present in the formulation at a concentration between 5% to 70% by weight;
   the nOSA starch to HP starch are present in the composition in a weight ratio of between 3:1 and 20:1; and
   2 percent by weight to 10 percent by weight of the composition is comprised of the starch blend; and
   the starch blend comprises 0.1 weight percent to 7 weight percent of the texturizer.

19. The composition of claim 18, wherein the texturizer comprises a sclaroglucan, a xanthan gum, or a mixture of both.

20. The composition of claim 18, wherein the weight ratio of nOSA starch to HP starch is between 3:1 and 10:1.

21. A cosmetic or personal care product comprising the composition of claim 18.

22. The cosmetic or personal care product of claim 21 selected from the group consisting of a skin protective cream, a lotion, a sunscreen, a skin or body cleanser, a skin conditioner, a skin toner, and a skin firming composition.

23. The cosmetic or personal care product of claim 22, wherein the cosmetic or personal care product is a sunscreen.

24. The composition of claim 18 comprising 30% to 60% by weight oil.

25. The composition of claim 21 comprising 50% to 60% by weight oil.

* * * * *

UNITED STATES PATENT AND TRADEMARK OFFICE
CERTIFICATE OF CORRECTION

PATENT NO. : 12,251,455 B2  
APPLICATION NO. : 17/440355  
DATED : March 18, 2025  
INVENTOR(S) : Nabila Belhaj et al.

Page 1 of 1

It is certified that error appears in the above-identified patent and that said Letters Patent is hereby corrected as shown below:

In the Claims

In Column 9, Claim 1, Line 11 delete "to" and insert -- and the --, therefor.
In Column 9, Claim 1, Line 12 after "ratio" insert -- of nOSA starch to HP starch --.
In Column 10, Claim 18, Line 8 delete "to" and insert -- and the --, therefor.
In Column 10, Claim 18, Line 8 after "of" insert -- nOSA starch to HP starch that is --.

Signed and Sealed this
Seventeenth Day of June, 2025

Coke Morgan Stewart
*Acting Director of the United States Patent and Trademark Office*